(12) United States Patent
Maschke

(10) Patent No.: US 8,506,492 B2
(45) Date of Patent: Aug. 13, 2013

(54) ULTRASOUND CATHETER AND IMAGING DEVICE FOR RECORDING ULTRA-SOUND IMAGES

(75) Inventor: Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 1347 days.

(21) Appl. No.: 11/411,742

(22) Filed: Apr. 26, 2006

(65) Prior Publication Data
US 2006/0264757 A1 Nov. 23, 2006

(30) Foreign Application Priority Data
Apr. 26, 2005 (DE) .......... 10 2005 019 371

(51) Int. Cl.
*A61B 8/14* (2006.01)
(52) U.S. Cl.
USPC ........... 600/463; 600/433; 600/435; 600/437; 600/466
(58) Field of Classification Search
USPC ................... 600/433, 466, 435, 437
See application file for complete search history.

(56) References Cited

U.S. PATENT DOCUMENTS

| 5,800,397 A | 9/1998 | Wilson et al. | |
|---|---|---|---|
| 5,989,208 A | 11/1999 | Nita | |
| 6,306,097 B1 * | 10/2001 | Park et al. | 600/466 |
| 6,461,303 B2 * | 10/2002 | Angelsen | 600/458 |
| 6,645,147 B1 * | 11/2003 | Jackson et al. | 600/458 |
| 6,764,450 B2 * | 7/2004 | Yock | 600/466 |
| 6,823,208 B2 * | 11/2004 | Ohlsson | 600/509 |
| 6,979,331 B2 * | 12/2005 | Hintringer et al. | 606/41 |
| 7,267,650 B2 * | 9/2007 | Chow et al. | 600/467 |
| 2002/0040185 A1 * | 4/2002 | Atalar et al. | 600/423 |
| 2004/0024371 A1 | 2/2004 | Plicchi et al. | |
| 2008/0200815 A1 * | 8/2008 | Van Der Steen et al. | 600/467 |

FOREIGN PATENT DOCUMENTS

| DE | 2500851 A1 | 6/1976 |
|---|---|---|
| DE | 27 58 040 A1 | 6/1979 |
| DE | 689 20 639 T2 | 12/1989 |
| DE | 695 32 639 T2 | 6/1997 |
| DE | 69630370 T2 | 2/1998 |
| DE | 69833854 T2 | 2/2000 |
| GB | 2 417 080 B * | 8/2004 |
| GB | 2417080 A * | 2/2006 |

* cited by examiner

Primary Examiner — Tse Chen
Assistant Examiner — Vani Gupta

(57) ABSTRACT

The invention relates to an ultrasound catheter comprising a device arranged in the area of the catheter tip for ultra-sound image recording, with at least one lumen routed into the area of the catheter tip open at this end and ending adjacent to the ultrasound image recording device for issuing an ultrasound contrast means being provided.

18 Claims, 2 Drawing Sheets

ULTRASOUND CATHETER AND IMAGING DEVICE FOR RECORDING ULTRA-SOUND IMAGES

CROSS REFERENCE TO RELATED APPLICATIONS

This application claims priority to the German application No. 10 2005 019 371.4, filed Apr. 26, 2005 which is incorporated by reference herein in its entirety.

FIELD OF INVENTION

The invention relates to an ultrasonic catheter and to an ultrasonic imaging device.

BACKGROUND OF INVENTION

Cardiovascular diseases, especially cardiac infarctions, are among the diseases which most frequently have fatal consequences. These infarctions are caused by diseases of the coronary arteries. In such cases atherosclerotic plaque results in a "blockage" of coronary arteries. In the majority of cases this is currently treated by a PCTA (Percutaneous Transluminal Coronary Angioplasty) which involves enlarging the constricted parts of the coronary arteries with a balloon catheter.

Further serious cardiological diseases are the tachycardial rhythm disturbances, e.g. atrial fibrillation. In this case atrioventicular disturbances in the heart mean that the ventricle is stimulated at high frequency. With other, e.g. ventricular tachycardias, there is no complete contraction and the result is an insufficient pumping power of the heart. These types of diseases are treated either through medicament or by an operation. The latter in particular is associated with a relatively high risk to the patient.

In recent times a minimally-invasive treatment method has become established. In such cases, depending on the pathology to be treated, a correspondingly designed catheter is introduced. For treating tachycardial rhythm disturbances for example an ablation catheter is introduced into the ventricle which for example uses electrical energy (high frequency) to "burn" the atrioventicular channels causing the problems. As explained above the appropriate catheters are used within the framework of the PCTA.

SUMMARY OF INVENTION

The treatments described above, using catheters are monitored with the aid of x-ray radiation and the support of x-ray contrast means, meaning that the position and movement of the medical instrument is continuously recorded. The disadvantage of x-ray monitoring lies in the fact that in this case the vessel diameter usable for blood flow or the constriction or also the heart chamber are only shown in silhouette.

The recording of a vessel using an ultrasound imaging device for the purposes of diagnostics or for catheter monitoring is further known. This imaging is undertaken using an ultrasound device from outside the body of which the ultrasound sensing head is placed on the body and positioned accordingly. To improve image contrast an ultrasound contrast means is introduced into the patient via a peripheral vessel. A difficulty here lies in the fact that the ultrasound contrast means now reaches the region of the body to be examined with a long time delay or around 30 seconds. A further disadvantage is the increased concentration or volume which has to be injected in order to see, since the contrast means is already breaking down again on its way through the blood vessel system. Nevertheless the ultrasound contrast means such as those based on sulfur hexafluoride, which form temporary gas bubbles in the blood stream and also improve the reflection characteristics of the ultrasound signals, contribute to improving the image quality.

As well as external ultrasound imaging the practice of recording ultrasound images directly from the interior of the blood vessels is also known using ultrasound catheters which have ultrasound recording equipment integrated on the catheter side. The disadvantage in this case is again however in particular the contrast behavior with such types of image recording. The use of an ultrasound contrast means which is introduced via a peripheral vessel also produces barely any improvements as regards the problems already described, especially as regards the ongoing breakdown of the contrast means.

DE 695 32 639 T2 describes an ultrasound imaging device with an ultrasound catheter, which, in what is known as a rotatable "nose element", features an acoustic imaging instrument for generating acoustic images of adjacent tissue. The ultrasound catheter has a transducer in its front area.

US 2004/0024371 A1 relates to a multi lumen catheter which ends in a needle system. The body of the catheter has at least two longitudinal lumina, via which liquids can be introduced with the aid of external means. These lumina of the catheter are connected to further longitudinal lumina of the needle system. In the catheter a tracer liquid which can also be a liquid used for ultrasound imaging is issued via the outflow opening of the needle itself.

A problem underlying the invention is that of specifying an ultrasound catheter which makes it possible to record ultrasound images with improved image quality, especially in contrast behavior.

The solution to this problem is provided for an ultrasound catheter of the type mentioned at the start in that at least one lumen routed into the area of the catheter tip open in this area and adjacent to the ultrasound image recording device is provided for issuing an ultrasound contrast means.

Unlike previously, when an inventive ultrasound catheter is used, the contrast means is not introduced in a location which is far from the actual image recording position, from where it has to sometimes cover a very long distance, with the associated disadvantages described, until it reaches the actual image recording position. Instead, in accordance with the invention, the ultrasound contrast means is supplied directly via the ultrasound catheter to the location in which the image is to be recorded so that it is present there at its maximum concentration thus meaning that the image recording improvements resulting from the addition of contrast means can be exploited to their full extent. A method for ultrasound image recording using such an ultrasound catheter stands out by virtue of the delivery of the ultrasound contrast means via the catheter-side lumen directly into the image recording area of the ultrasound image recording device.

The opening of the lumen in relation to the catheter tip can lie before the ultrasound imaging device. As an alternative to this the one lumen can end in at least two openings of which one lies before the other after the ultrasound imaging device. A further inventive alternative makes provision for two or more lumina each ending in one opening which lie before and after the ultrasound imaging device. Depending on the design of the catheter or of the vessel accepting it, this enables the optimum supply option for the ultrasound contrast means to be used.

Furthermore a connection device for connecting the lumen or lumina is expediently provided at an injection device for automatic injection of the contrast means. The delivery of the contrast means here with such an ultrasound catheter device consisting of the ultrasound catheter and injection device is not undertaken manually but under automatic control, so that a highly accurate dosing of the contrast means delivery is possible.

Since ultrasound catheters are also monitored during their movement through the vessel by an x-ray device, a further advantageous embodiment of the invention makes provision for the embodiment of at least one further lumen directed into the area of the catheter tip opening out in at least one opening at this tip for delivery of an x-ray contrast means, so that the detectability of the catheter tip during the x-ray monitoring is at its optimum as a result of the direct issuing of the x-ray contrast means in the catheter tip area. In this case a connection device can also be provided for connecting the further lumen or lumina to an injection device for automatic injection of the x-ray contrast means, so that here too an optimum dosing is possible. In this case a shared connection device can naturally be provided via which both the ultrasound contrast means and also the X-ray contrast means can be supplied to the relevant lumina in a controlled manner.

As well as the ultrasound image recording device it is naturally also possible to provide other imaging sensors (e.g. an OCT sensor) or other sensors or device s for recording information or for handling information at the catheter, for example ablation electrodes, triggering or stimulation electrodes or devices for delivering radiation etc. Furthermore the corresponding sensors or devices (for example optical magnetic, electromagnetic or acoustic) can be provided for finding the position of the catheter or of the catheter tip. Facilities for controlling the catheter or catheter tip, for example mechanical, magnetic, electromagnetic or piezoelectric devices can also be integrated into the catheter to control a catheter and of course an x-ray marker can be provided directly on the catheter shaft.

Furthermore it is conceivable to apply an outer coating to a catheter which reduces its frictional resistance while it is being guided through the vessel. Such a coating can for example be a nanoparticle coating or a hydrophilic layer made of Silicon. Furthermore it is also conceivable to use nanotechnology to apply a thin-film layer made of conductive nanoparticles (e.g. silicon dioxide, aluminum dioxide, silicon nitrate or carbon nanoparticles) which make it possible to use the catheter in a magnetic resonance system or a system for magnetic navigation without disruption and without endangering the patient, since this thin-film layer can be used to provide magnetic shielding.

In addition to the ultrasound catheter itself the invention further relates to an image recording device for recording at least ultrasound images, comprising a catheter of the type described above as well as a control device connected to the catheter-side ultrasound imaging device which controls the operation of the ultrasound imaging device and is simultaneously used for generating and outputting the ultrasound images.

Furthermore an injection device for automatically injecting the ultrasound contrast means can be provided which is controlled via the control device so that the delivery of the ultrasound contrast means and the actual image recording can be correlated or synchronized in time. Furthermore another injection device can be provided if necessary for automatic injection of the x-ray contrast means which is preferably also controlled via the control device so that an optimized x-ray image recording can be undertaken via an x-ray device operating in parallel. Of course it is possible to couple the control device of the ultrasound imaging device to the control device of the x-ray device so that the operation of the injection device for delivering the x-ray contrast means is correlated in time or synchronized with the recording operation of the x-ray device and so that x-ray contrast means is delivered at precisely the point in time at which it must be present in the vessel or such like for x-ray imaging.

Expediently a device is also provided for ECG or breathing recording which communicates with the control device which then controls one or both of the injection devices as a function of the result of the recording. An ECG or breathing triggering of the injection devices can also be controlled via this device. For example it is useful for a specific recording to only deliver the ultrasound and/or the x-ray contrast means at a specific phase of the heart, for example in the inactive phase, a process which is able to be easily controlled if ECG triggering is used.

An especially advantageous further development of the invention makes provision for a means of selection, which communicates with the control device, to be able to select the delivery of the ultrasound contrast means, with the control device automatically accessing image recording or image processing parameters stored in the control device depending of the ultrasound contrast means selected and controlling further operation on the basis of this. Since the way in which different contrast means operate is not always the same the resulting image quality is at least also partly dependent on the contrast means. The image quality can, since the effect or operation of the contrast means is known per se, be improved however by using recording and/or image processing parameters which are optimized for a specific contrast means to record or generate the images. These are now usefully stored on the control device side so that they can be retrieved from a corresponding memory. To record the image the physician now for example selects on a monitor using a suitable means of input the ultrasound contrast means to be used (monitor and means of input then for example form the selection means) after which the control device automatically downloads the parameters specific to the corresponding contrast means and continues operation using these parameters. The corresponding parameters in this case in particular take account of the different gas bubble formation (one contrast means forms more and the other fewer bubbles) but also the very wide variety of decay times of the gas bubbles formed etc.

A further development of the inventive idea makes provision, with a means of recording, for an identification code to be provided on the ultrasound catheter and/or on a container containing the ultrasound contrast means, especially in the form of a bar code or of an RFID transponder, in which case the control device, depending on the result of the recording, automatically accesses catheter or contrast means-specific image recording and/or image processing parameters stored in the control device and controls further operation on the basis of these parameters. If for example a corresponding identification code is arranged on the ultrasound catheter, the control device then recognizes, when this identification code is passed over by a corresponding reader device, automatically that an ultrasound catheter image recording is due, so that the corresponding parameters can already be preset. Equally a contrast means can be recognized in this way on read-out of the container-side identification and the corresponding parameters preset. This recording also provides the opportunity to enable the catheter and the contrast means to be traced better within the logistics chain of the hospital for example.

Finally a further embodiment of the invention makes provision for contrast means—specific decay curves to be arranged in the control device, in which case the control device is embodied for image processing on the basis of the decay curves and the energy or power controlled via the control device issued by the ultrasound image recording device. This allows optimization of the image processing in real time to be undertaken automatically since the time-related decay is recognized via the decay curve and for example the ultrasound power output can be increased with increasing decay in order to compensate for the reflection properties which are deteriorating as decay increases, by increasing the power.

BRIEF DESCRIPTION OF THE DRAWINGS

Further advantages, features and details of the invention are produced by the exemplary embodiment described below, as well with reference to the drawings. The Figures show.

DETAILED DESCRIPTION OF INVENTION

Figure 1:
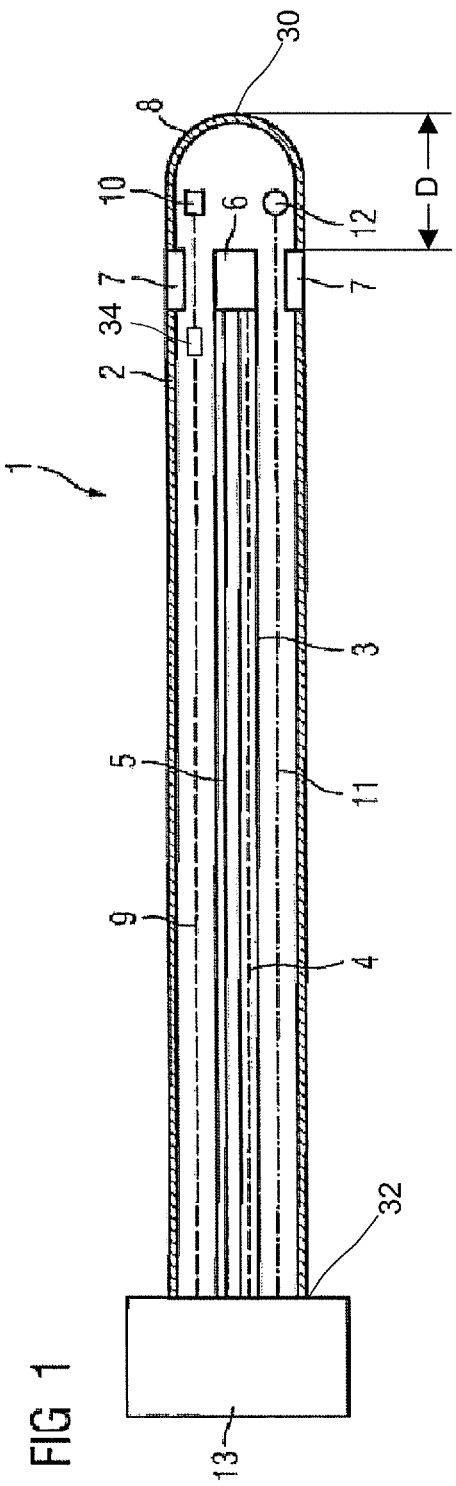
FIG. 1 a basic diagram of an inventive ultrasound catheter.

FIG. 1 shows an inventive ultrasound catheter 1, consisting of the catheter sleeve 2, in which a first lumen 3 is provided, in which are guided the signal line 4 and also a drive shaft 5 for rotational drive of an ultrasound image recording device 6, i.e. of an ultrasound sensor (e.g. of an IVUS sensor) which is accommodated at the end of lumen 3 so that it can rotate. On the catheter sleeve 2 opposite the ultrasound imaging device 6 are arranged, one or more windows 7 transparent for ultrasound, from which the ultrasound signals issued by the ultrasound image recording device 6 exit, and via which the reflection signals reflected off the vessel wall or similar enter the image recording de vice 6 again. It can be seen that the ultrasound image recording device 6 is provided in the area of the rounded catheter tip 8 here.

A lumen 9 is further provided which is embodied inside the catheter 1 or the catheter sleeve 2 and which leads to an opening 10 which opens out in the area of the catheter tip 8, here directly in before the ultrasound image recording device 6. Ultrasound contrast media can be fed via the lumen 9 and the opening 10 and issued in the area of the vessel immediately before the ultrasound image recording device 6. It is naturally possible not only to provide an opening 10 but to provide several openings distributed radially which are coupled accordingly to the lumen 9, as well as of course for a number of lumina 9 to be able to run in parallel and distributed radially to the catheter tip and to open out in corresponding openings. It is conceivable to provide additional corresponding openings 10 after the ultrasound image recording device 6, so that this can be washed around on both sides by ultrasound contrast means.

As shown in FIG. 1, catheter sleeve 2 axially-extends from a proximate end 32 to a distal end 30 of the catheter and is configured to define an interior space of the catheter. As noted above, window 7 is positioned opposite ultrasonic imaging device 6 to allow ultrasound signals to pass through. As shown in FIG. 1, ultrasonic device 6 and window 7 are positioned to be spaced apart (e.g., distance D) from the distal end 30 of the catheter. Lumen 9 axially extends within the interior space of the catheter defined by axially-extending catheter sleeve 2 to a location disposed between distal end 30 of the catheter and ultrasonic imaging device 6 and window 7. Lumen 9 has opening 10 at the location disposed between distal end 30 and ultrasonic imaging device 6 and window 7. As can be appreciated in FIG. 1, end opening 10 is configured to release an ultrasonic contrast agent at a location axially forward of the ultrasonic imaging device 6 and window 7. In another example embodiment, a second opening 34 may be provided in lumen 9 (or in a further lumen) to release the ultrasonic contrast agent at a location axially rearward of ultrasonic imaging device 6 and window 7.

Finally a further lumen 11 is provided which is embodied in the catheter sleeve and which also runs into the area of the catheter tip 8 and opens out into an opening 12 there. This lumen 11 is used for supplying and issuing an x-ray contrast means in the area of the catheter tip, so that in a parallel x-ray monitoring the catheter tip can be recorded in the optimum way as a result of the high contrast means concentration.

Furthermore there is provision for a connecting device 13, in which the signal line 4, the drive shaft 5 and also the lumen 9 and 11 all terminate. This connecting device has corresponding mechanical and electrical connection means for coupling to the control device not shown in any greater detail here as well as corresponding ultrasound and x-ray contrast media injectors.

Figure 2:
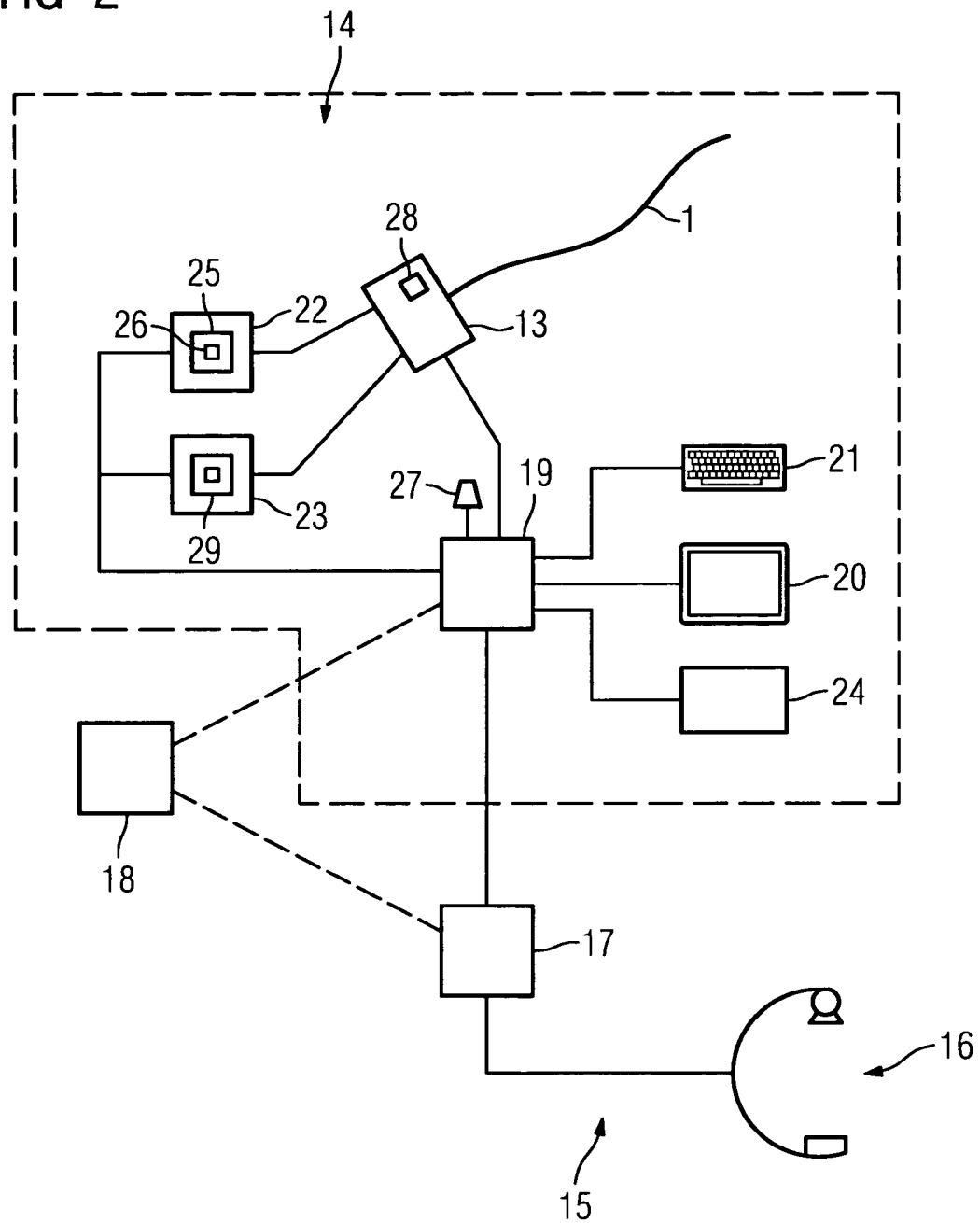
FIG. 2 a basic outline diagram of an inventive ultrasound image recording device.

FIG. 2 shows an inventive image recording device 14 which is delineated by the dashed line. This image recording device 14 is an x-ray device 15 used for simultaneous x-ray monitoring of the ultrasound catheter 1 introduced into the patient and comprises an x-ray recording means 16, usually consisting of a radiographic source and a radiographic detector, and also assigned to a control device 17, as well as, in the example shown here, a central patient database 18.

The image recording device 14 comprises on the one hand the ultrasound catheter 1 already described. Connected to the connection device 13 in the example shown is first a control device 19, which controls the image recording operation of the ultrasound image recording device 6 as well as its rotational drive. A monitor 20, and also a means of input 21 in the form of a keyboard, are assigned to the control device 19.

Furthermore two injectors 22, 23 are provided at the corresponding connections of the connection device 13, which each contain containers 25, 29 with an ultrasound contrast means (for example the injector 22) or an x-ray contrast means (for example the injector 23). These contrast means can be supplied via corresponding lines, which come out at the connection device 13 and go over into the catheter-side lumen 9 or 11, so that if required they come out at the corresponding openings 10 or 12. The operation of the injector 22, 23 is also controlled via the control device 19.

Furthermore a device 24 for deriving an ECG or for recording the breathing movement is provided, which also communicates with the control device 19. An ECG-triggered activation of the corresponding injectors 22 and/or 23 can be undertaken using this device for example, so that the relevant contrast means is only supplied during a specific heart cycle for example. The device 24 can alternatively also serve to record blood pressure, so that it is possible to used blood pressure as a trigger for supply of contrast means.

As FIG. 2 shows, the control device 19 continues to be connected to the control device 17 of the x-ray device 15. The injector 23 supplying the contrast means can also be triggered by this device, namely at the point in time at which an x-ray image is actually to be recorded, so that it is ensured that the x-ray contrast means is present in a high concentration in the catheter tip area.

Furthermore the control device 19 and also the control device 17 are coupled to the patient database 18, so that corresponding patient data which is required in any particular form for control operation is present on the relevant control device side.

In operation the physician now initially uses the input means 21 to select for example from a list displayed to him on the monitor 20 of individual contrast means which are stored in a corresponding memory on the control device 19, the contrast means which is subsequently actually to be supplied. The control device 19 then automatically loads the image recording and/or image processing parameters, which are stored for specific contrast means in a corresponding memory on the control device 19 side, in order to ensure a contrast-means-specific optimum image recording and image generation. This is especially true in relation to the ultrasound contrast means.

As an alternative to selection by the user via the monitor 20 there is the option of automatically recording the ultrasound contrast means to be supplied. For this purpose an identification label 26, e.g. a bar code or an RFID responder is arranged for example on the container 25 containing the ultrasound contrast means, with this identification label able to be read out using a corresponding reader 27 which communicates with the control device 19. This allows the contrast means type used to be detected exactly, so that the corresponding image recording and/or image processing parameters can be loaded in. This also applies in relation to the ultrasound catheter 1, this too can have a corresponding identification label 28, which can be read out accordingly so that the catheter type used can be automatically detected in this way or the corresponding image recording device as well as the operating and performance parameters can be recorded, which is also important for optimization of image recording and image generation. Parameters corresponding to specific catheters can then be loaded in on the control device 19 side and re-used.

Overall the use of the inventive ultrasound catheter allows optimum supply of ultrasound contrast means directly to the location at which the image is recorded, so that a marked improvement in intracorporal ultrasound imaging as a result of the high contrast means concentration provided at the actual point of image recording is achieved. The same applies where parallel x-ray monitoring is undertaken, as a result of the supply of x-ray contrast means directly into the catheter tip area. Furthermore the inventive image recording device allows optimized contrast means supply as well as image recording and image processing, since by using the appropriate injectors an automatic, exactly controllable contrast means supply and in addition, if required an exact synchronization of the supply as well as triggering is possible.

The invention claimed is:

1. An ultrasonic catheter, comprising:
   a closed-ended catheter sleeve axially-extending from a proximate end to a distal closed-end of the catheter, the catheter sleeve configured for travel in a passageway defined by a blood vessel;
   an ultrasonic imaging device for generating an ultrasonic image, the ultrasonic imaging device arranged at a tip of the catheter, the closed-ended catheter sleeve including at least one window positioned opposite the ultrasonic imaging device to allow ultrasound signals to pass through, the ultrasonic device and said at least one window positioned to be spaced apart from the distal closed-end of the catheter;
   at least one lumen arranged in the closed-ended catheter and adjacent to the ultrasonic imaging device, said at least one lumen axially extending and fully contained within an interior space of the axially-extending closed-ended catheter sleeve to a location disposed between the closed-distal end of the catheter and the ultrasonic imaging device and said at least one window, said at least one lumen having at least one end opening at the location disposed between the distal closed-end of the catheter and the ultrasonic imaging device and said at least one window, the end opening disposed on a surface of the axially-extending closed-ended catheter sleeve at a location axially forward of the ultrasonic imaging device and said at least one window and configured to release an ultrasonic contrast agent at said axially forward location;
   an injector arranged to automatically inject the ultrasonic contrast agent into said at least one lumen;
   a computerized control device coupled to the ultrasonic imaging device and the injector, the control device configured to synchronize in a time domain an injection of the ultrasonic contrast agent with respect to a recording of the ultrasonic image.

2. The catheter in accordance with claim 1, wherein the lumen has a second end opening, the second end opening disposed on the surface of the axially-extending catheter sleeve at a location axially rearward of the ultrasonic imaging device and said at least one window and arranged to release the ultrasonic contrast agent at said axially rearward location.

3. The catheter in accordance with claim 1, wherein the catheter further comprises a second lumina having a respective end opening disposed on the surface of the axially-extending catheter sleeve at a location axially rearward of the ultrasonic imaging device and said at least one window and arranged to release an ultrasonic contrast agent at said axially rearward location.

4. The catheter in accordance with claim 1, further comprising a connector for connecting the at least one lumen to the injector, the injector responsive to a signal from the control device to automatically inject the ultrasonic contrast agent.

5. The catheter in accordance with claim 1, further comprising at least one further lumen routed up to the tip and having at least one opening for releasing an x-ray contrast agent.

6. The catheter in accordance with claim 5, further comprising a further connector for connecting the further lumen to a further injector, the further injector responsive to a signal from the control device to automatically inject the x-ray contrast agent.

7. The catheter in accordance with claim 6, wherein the connector and the further connector are integrated into a common connector.

8. An image recording device for recording at least ultrasound images, comprising:
   an ultrasonic catheter, comprising:
      a close-ended catheter sleeve axially extending from a proximate end to a distal closed-end of the catheter, the catheter sleeve configured for travel in a passageway defined by a blood vessel;
   an ultrasonic imaging device for generating an ultrasonic image, the ultrasonic imaging device arranged at a tip of the catheter, the catheter sleeve including at least one window positioned opposite the ultrasonic imaging device to allow ultrasound signals to pass through, the ultrasonic device and said at least one window positioned to be spaced apart from the distal closed-end of the catheter; and
   at least one lumen arranged in the catheter and adjacent to the ultrasonic imaging device, said at least one lumen axially extending and fully contained within an interior space of the close-ended catheter sleeve to a location disposed between the closed-distal end of the catheter and the ultrasonic imaging device and said at least one window, said at least one lumen having at least one end opening at the location disposed between the closed-distal end of the catheter and the ultrasonic imaging device and said at least one window, the end opening disposed on a surface of the axially-extending closed-ended catheter sleeve and located axially forward of the ultrasonic imaging device and said at least one window and arranged to release an ultrasonic contrast agent axially forward of the ultrasonic imaging device and said at least one window;

an injector arranged to automatically inject the ultrasonic contrast agent into said at least one lumen;

a computerized control device connected to the injector and the ultrasonic imaging device for generating and outputting the ultrasonic image, the control device further configured to synchronize in a time domain an injection of the ultrasonic contrast agent with respect to a recording of the ultrasonic image.

9. The device in accordance with claim 8, wherein the lumen has a second end opening disposed on the surface of the axially-extending catheter sleeve at a location axially rearward of the ultrasonic imaging device and said at least one window and arranged to release the ultrasonic contrast agent axially rearward of the ultrasonic imaging device and said at least one window.

10. The device in accordance with claim 8, wherein the catheter further comprises a second lumina having a respective end opening disposed on the surface of the axially-extending catheter sleeve at a location axially rearward of the ultrasonic imaging device and said at least one window and arranged to release the ultrasonic contrast agent axially rearward of the ultrasonic imaging device and said at least one window.

11. The device in accordance with claim 8, wherein the injector is controlled in response to a signal from the control device.

12. The device in accordance with claim 8, further comprising a further injector configured to automatically inject an x-ray contrast agent, the further injector controlled in response to a signal from the control device.

13. The device in accordance with claim 11, further comprising a medical device for acquiring an ECG, a breathing or a blood pressure of a patient, the medical device connected to the control device, wherein the injector is controlled by the control device based upon the acquired ECG, breathing or blood pressure.

14. The device in accordance with claim 12, further comprising a medical device for acquiring an ECG, a breathing or a blood pressure of a patient, the medical device connected to the control device, wherein the further injector is controlled by the control device based upon the acquired ECG, breathing or blood pressure.

15. The device in accordance with claim 8, wherein the ultrasonic contrast agent is selected by a selection unit connected to the control device, the control device configured to automatically access contrast agent-specific image recording or image processing parameters stored in the control device based on the selected ultrasonic contrast agent.

16. The device in accordance with claim 8, further comprising a reader for reading an identification label arranged on or at the ultrasound catheter, wherein the control device is configured to automatically access catheter-specific or contrast agent-specific image recording or image processing parameters stored in the control device based upon the read identification label.

17. The device in accordance with claim 16, wherein the identification label is a bar code or an RFID transponder.

18. The device in accordance with claim 8, wherein contrast agent-specific decay curves are stored in the control device, the control device configured for image processing based on the decay curves and based upon an energy emitted by the ultrasonic imaging device.

* * * * *